United States Patent
Yagi et al.

(10) Patent No.: US 9,548,463 B2
(45) Date of Patent: Jan. 17, 2017

(54) ORGANIC PHOTOELECTRONIC DEVICE AND IMAGE SENSOR

(71) Applicant: Samsung Electronics Co., Ltd., Suwon-si, Gyeonggi-do (KR)

(72) Inventors: Tadao Yagi, Hwaseong-si (KR); Rie Sakurai, Suwon-si (KR); Kyung-bae Park, Hwaseong-si (KR); Sung Young Yun, Suwon-si (KR); Gae Hwang Lee, Seongnam-si (KR); Kwang Hee Lee, Yongin-si (KR); Dong-Seok Leem, Hwaseong-si (KR); Xavier Bulliard, Seongnam-si (KR); Chul Joon Heo, Busan (KR); Yong Wan Jin, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 53 days.

(21) Appl. No.: 14/587,394

(22) Filed: Dec. 31, 2014

(65) Prior Publication Data

US 2016/0020415 A1    Jan. 21, 2016

(30) Foreign Application Priority Data

Jul. 21, 2014  (KR) .................. 10-2014-0092001

(51) Int. Cl.
*H01L 51/00*  (2006.01)
*C07F 7/08*  (2006.01)
(Continued)

(52) U.S. Cl.
CPC ......... *H01L 51/0094* (2013.01); *C07F 7/0834* (2013.01); *H01L 51/008* (2013.01);
(Continued)

(58) Field of Classification Search
CPC ............... H01L 51/008; H01L 51/0046; H01L 51/4253; H01L 51/442
See application file for complete search history.

(56) References Cited

U.S. PATENT DOCUMENTS

| 7,973,307 B2 | 7/2011 | Rand et al. |
| 2012/0090685 A1 | 4/2012 | Forrest et al. |

(Continued)

FOREIGN PATENT DOCUMENTS

| JP | 2011-140639 A | 7/2011 |
| JP | 5296674 B2 | 9/2013 |
| WO | WO-9424612 | 10/1994 |

OTHER PUBLICATIONS

Graham E. Morse et al., "Phthalimido-boronsubphthalocyanines: New Derivatives of; Boronsubphthalocyanine with Bipolar Electrochemistry and; Functionality in OLEDs.", Applied Materials & Interfaces, American Chemical Society, 2011, pp. 3538-3544.
(Continued)

*Primary Examiner* — Mamadou Diallo
(74) *Attorney, Agent, or Firm* — Harness, Dickey & Pierce, P.L.C.

(57) ABSTRACT

Example embodiments relate to an organic photoelectronic device including a first electrode and a second electrode facing each other, and an active layer between the first electrode and the second electrode, wherein the active layer
(Continued)

includes a first compound represented by the following Chemical Formula 1, and an image sensor including the organic photoelectronic device.

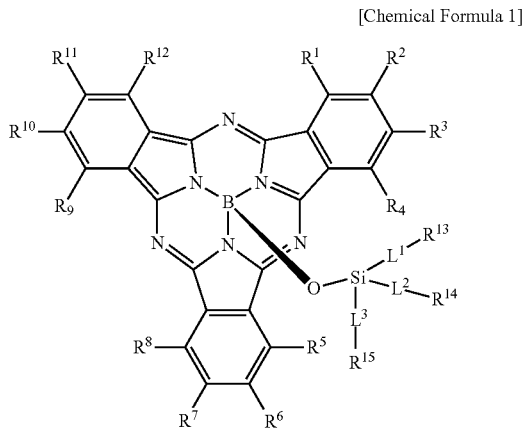

[Chemical Formula 1]

14 Claims, 11 Drawing Sheets

(51) Int. Cl.
H01L 27/30 (2006.01)
H01L 51/44 (2006.01)
H01L 51/42 (2006.01)

(52) U.S. Cl.
CPC .......... H01L 27/301 (2013.01); H01L 27/307 (2013.01); H01L 51/0046 (2013.01); H01L 51/4253 (2013.01); H01L 51/442 (2013.01); H01L 2251/308 (2013.01)

(56) References Cited

U.S. PATENT DOCUMENTS

2013/0270545 A1* 10/2013 Tanaka .................. B82Y 10/00 257/40
2014/0160327 A1 6/2014 Enoki et al.
2015/0129861 A1* 5/2015 Hamano ............. H01L 51/0061 257/40

OTHER PUBLICATIONS

Julia Guilleme et al., "Triflate-Subphthalocyanines: Versatile, Reactive Intermediates for Axial Functionalization at the Boron Atom", Aromatic Macrocycles, Wiley Online Library, 2011, pp. 3506-3509.
Graham E. Morse et al., "Aluminum Chloride Activation of Chloro-Boronsubphthalocyanine: a; Rapid and Flexible Method for Axial Functionalization with an Expanded Set of Nucleophiles", Inorganic Chemistry) ACS Publications, 2012, pp. 6460-6467.
Mabel V. Fulford et al., "Crystal Structures, Reaction Rates, and Selected Physical Properties of Halo-Boronsubphthalocyanines (Halo = Fluoride, Chloride, and Bromide)", Journal of Chemical Engineering & Data, ACS Publications, 2012, pp. 2756-2765.
Jeremy D. Dang et al., A Boron Subphthalocyanine Polymer Poly(4-rnethylstyrene)-copoly(;phenoxy boron subphthalocyanine), ACS Publications, American Chemical Society, 2012, pp. 7791-7798.
Biwu Ma et al, "Solution processable boron subphthalocyanine derivatives as active materials for organic photovoltaics", Organic Photovoltaics X, Proc. of SPIE vol. 7416, pp. 1-6.
Satoshi Aihara et al., "Stacked Image SensorWith Green- and Red-Sensitive; Organic Photoconductive Films Applying Zinc Oxide; Thin-Film Transistors to a Signal Readout Circuit", IEEE Transactions on Electron Devices, vol. 56, No. 11, Nov. 2009, pp. 2570-2576.
Hokuto Seo et al., "Colo Sensors with Three Vertically Stacked Organic Photodetectors", Japanese Journal of Applied Physics, vol. 46, No. 49, 2007, pp. L1240-L1242.
CAS Registry, XP55232087, C:\\EPODATA\SEA\eplogf\EP15162784.log, Nov. 27, 2015.
Cate, Michael C., "Kinetics of the Ligand Exchange Reactions Between Bidentate Ligands and Triethylenetetramine Nickelate (II) and Synthesis of Boron (III) Subphthalocyanines with Various Boron Substitutions," Eastern Michigan University, Apr. 1, 2007, Paper 43, pp. 1-88.
Claessens, Christian G., et al., "Subphthalocyanines, Subporphyrazines, and Subporphyrins: Singular Nonplanar Aromatic Systems," American Chemical Society—Chemical Reviews, vol. 114, No. 4, Feb. 26, 2014, pp. 2192-2277.
Lin, Chi-Feng, et al., "Chloroboron subphthalocyanine/C60 planar heterojunction organic solar cell with N, N-dicarbazolyl-3,5-benzene blocking layer," Solar Energy Materials & Solar Cells, Elsevier Science Publisher, Amsterdam, NL, vol. 122, Jan. 3, 2014, pp. 264-270.
Lessard, Benoît H., "Bis(tri-n-hexylsilyl oxide) Silicon Phthalocyanine: A Unique Additive in Ternary Bulk Heterojonction Organic Photovoltaic Devices," American Chemical Society—Applied Materials & Interfaces, vol. 6, Aug. 22, 2014, pp. 15040-15051.
European Search Report mailed on Dec. 8, 2015.

* cited by examiner

ORGANIC PHOTOELECTRONIC DEVICE AND IMAGE SENSOR

RELATED APPLICATIONS

This application claims the benefit of priority from Korean Patent Application No. 10-2014-0092001, filed in the Korean Intellectual Property Office on Jul. 21, 2014, the entire contents of which are incorporated herein by reference.

BACKGROUND

1. Field

Example embodiments relate to an organic photoelectronic device and/or an image sensor.

2. Description of the Related Art

A photoelectronic device typically converts light into an electrical signal using photoelectronic effects, and may include a photodiode, a phototransistor, and the like, and it may be applied to an image sensor, a solar cell, and the like.

An image sensor including a photodiode requires typically high resolution and thus a small pixel. At present, a silicon photodiode is widely used, but exhibits deteriorated sensitivity because of a small absorption area due to the small pixels. Accordingly, an organic material that is capable of replacing silicon has been researched.

The organic material has a high extinction coefficient and selectively absorbs light in a particular wavelength region depending on a molecular structure, and thus may simultaneously replace a photodiode and a color filter, and as a result improve sensitivity and contribute to high integration.

SUMMARY

At least one example embodiment relates to an organic photoelectronic device configured to increase wavelength selectivity and decrease crosstalk between each pixel by improving light absorption characteristics in a thin film state.

Another example embodiment relates to an image sensor including the organic photoelectronic device.

According to one example embodiment, an organic photoelectronic device includes a first electrode and a second electrode facing each other, and an active layer interposed between the first electrode and the second electrode, wherein the active layer includes a first compound represented by the following Chemical Formula 1.

[Chemical Formula 1]

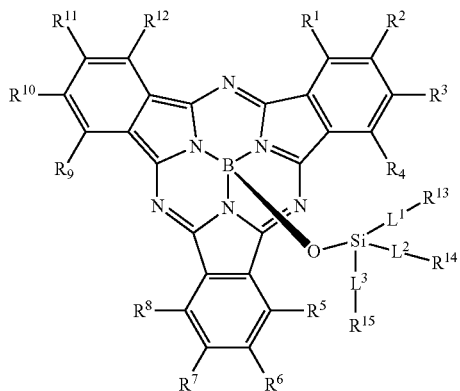

In the above Chemical Formula 1, $R^1$ to $R^{12}$ are independently hydrogen or a monovalent organic group, $R^1$ to $R^{12}$ are independently present or form a ring, and $L^1$ to $L^3$ are independently a single bond or a divalent organic group, $R^{13}$ to $R^{15}$ are independently a substituted or unsubstituted C1 to C30 alkyl group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group, a substituted or unsubstituted C6 to C30 arylamine group, a substituted or unsubstituted silyl group, or a combination thereof.

According to at least one example embodiment, $R^1$ to $R^{12}$ are independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C1 to C30 aryloxy group, a thio group, an alkylthio group, an arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, or a combination thereof, and $L^1$ to $L^3$ are independently a single bond, a substituted or unsubstituted C1 to C30 alkylene group, a substituted or unsubstituted C6 to C30 arylene group, a divalent substituted or unsubstituted C3 to C30 heterocyclic group, or a combination thereof.

The first compound represented by Chemical Formula 1 may selectively absorb light in a green wavelength region.

The first compound may have a maximum absorption wavelength ($\lambda_{max}$) of about 500 nm to about 600 nm.

The active layer may further include a second compound absorbing light in a visible ray region.

The second compound may include fullerene or a fullerene derivative.

The second compound may include thiophene or a thiophene derivative.

The active layer may show a light absorption curve having a full width at half maximum (FWHM) of less than or equal to about 80 nm.

The first electrode and the second electrode may respectively be a transparent electrode.

According to another example embodiment, an image sensor including the organic photoelectronic device is provided.

The image sensor may include a semiconductor substrate integrated with a plurality of first photo-sensing devices sensing light in a blue wavelength region and a plurality of second photo-sensing devices sensing light in a red wavelength region, and the organic photoelectronic device positioned on the semiconductor substrate and selectively absorbing light in a green wavelength region.

The first photo-sensing device and the second photo-sensing device may be stacked in a vertical direction on the semiconductor substrate.

The image sensor may further include a color filter layer positioned between the semiconductor substrate and the organic photoelectronic device, and including a blue filter selectively absorbing light in a blue wavelength region, and a red filter selectively absorbing light in a red wavelength region.

The image sensor may include a green photoelectronic device of the organic photoelectronic device, a blue photoelectronic device selectively absorbing light in a blue wavelength region, and a red photoelectronic device selectively absorbing light in a red wavelength region and that are stacked.

According to another example embodiment, the compound represented by the above Chemical Formula 1 is provided.

The compound represented by the above Chemical Formula 1 may be configured to selectively absorb light in a green wavelength region.

DETAILED DESCRIPTION

Figure 1:
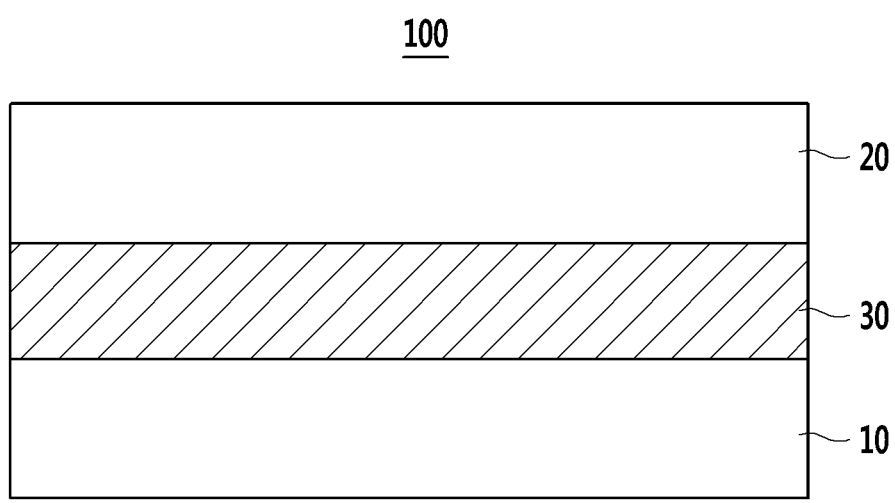
FIG. 1 is a cross-sectional view showing an organic photoelectronic device according to at least one example embodiment.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

Example embodiments will hereinafter be described in detail, and may be easily performed by those who have common knowledge in the related art. However, this disclosure may be embodied in many different forms and is not construed as limited to the example embodiments set forth herein.

As used herein, when a definition is not otherwise provided, the term "substituted" refers to one substituted with a substituent such as a halogen (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof, instead of hydrogen of a compound.

As used herein, when specific definition is not otherwise provided, the term "hetero" refers to one including 1 to 3 heteroatoms such as N, O, S, and P.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

Hereinafter, a compound for an organic photoelectronic device according to at least one example embodiment is described.

A compound for an organic photoelectronic device according to at least one example embodiment is represented by the following Chemical Formula 1.

[Chemical Formula 1]

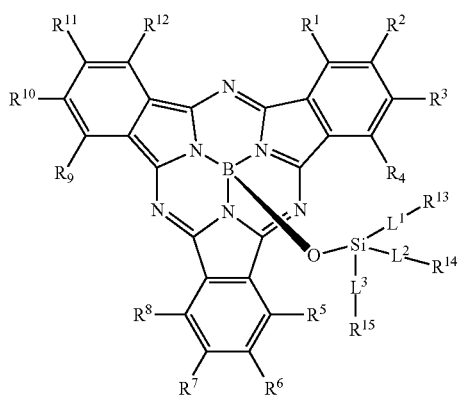

In the above Chemical Formula 1, $R^1$ to $R^{12}$ are independently hydrogen or a monovalent organic group, $R^1$ to $R^{12}$ are independently present or form a ring, $L^1$ to $L^3$ are independently a single bond or a divalent organic group, and $R^{13}$ to $R^{15}$ are independently a substituted or unsubstituted C1 to C30 alkyl group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group, a substituted or unsubstituted C6 to C30 arylamine group, a substituted or unsubstituted silyl group, or a combination thereof.

For example, $R^1$ to $R^{12}$ may independently be hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C1 to C30 aryloxy group, a thio group, an alkylthio group, an arylthio group, a cyano group, a cyano-containing group, a halogen group, a halogen atom, a halogen-containing group, a substituted or unsubstituted sulfonyl group, a substituted or unsubstituted aminosulfonyl group, a substituted or unsubstituted arylsulfonyl group, or a combination thereof, but are not limited thereto.

For example, $L^1$ to $L^3$ may independently be a single bond, a substituted or unsubstituted C1 to C30 alkylene group, a substituted or unsubstituted C6 to C30 arylene group, a divalent substituted or unsubstituted C3 to C30 heterocyclic group, or a combination thereof, but are not limited thereto.

The compound represented by the above Chemical Formula 1 may be configured to selectively absorb light in a green wavelength region, and may have, for example, a maximum absorption wavelength ($\lambda_{max}$) at about 500 nm to 600 nm.

Hereinafter, an organic photoelectronic device including the compound is described referring to the drawings.

FIG. 1 is a cross-sectional view of an organic photoelectronic device according to at least one example embodiment.

Referring to FIG. 1, an organic photoelectronic device 100 according to at least one example embodiment includes a first electrode 10 and a second electrode 20, and an active layer 30 between the first electrode 10 and the second electrode 20.

One of the first electrode 10 and the second electrode 20 may be an anode and the other may be a cathode. At least one of the first electrode 10 and the second electrode 20 may be a light-transmitting electrode, and the light-transmitting electrode may include, for example, a transparent conductor such as indium tin oxide (ITO) or indium zinc oxide (IZO), or a metal thin layer of a thin monolayer or multilayer. When one of the first electrode 10 and the second electrode 20 is a non-light-transmitting electrode, the first electrode 10 and the second electrode 20 may include, for example, an opaque conductor such as aluminum (Al).

For example, the first electrode 10 and the second electrode 20 may be light-transmitting electrodes.

The active layer 30 may include a p-type semiconductor material and an n-type semiconductor material to form a pn junction, and may absorb external light to generate excitons and then may separate the generated excitons into holes and electrons.

The example active layer 30 includes a first compound represented by the following Chemical Formula 1.

[Chemical Formula 1]

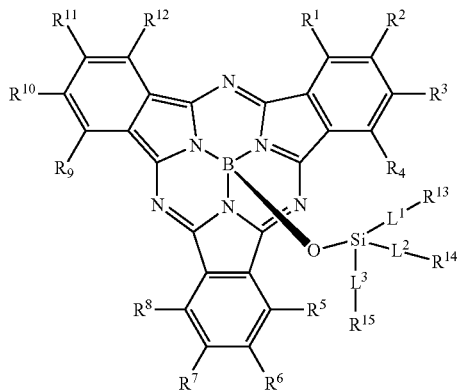

In the above Chemical Formula 1, $R^1$ to $R^{12}$ are independently hydrogen or a monovalent organic group, $R^1$ to $R^{12}$ are independently present or form a ring, $L^1$ to $L^3$ are independently a single bond or a divalent organic group, and $R^{13}$ to $R^{15}$ are independently a substituted or unsubstituted C1 to C30 alkyl group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group, a substituted or unsubstituted C6 to C30 arylamine group, a substituted or unsubstituted silyl group, or a combination thereof.

For example, $R^1$ to $R^{12}$ may independently be hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C1 to C30 aryloxy group, a thio group, an alkylthio group, an arylthio group, a cyano group, a cyano-containing group, a halogen atom, a halogen-containing group, a substituted or unsubstituted sulfonyl group, a substituted or unsubstituted aminosulfonyl group, a substituted or unsubstituted arylsulfonyl group, or a combination thereof, but are not limited thereto.

For example, $L^1$ to $L^3$ may independently be a single bond, a substituted or unsubstituted C1 to C30 alkylene group, a substituted or unsubstituted C6 to C30 arylene group, a divalent substituted or unsubstituted C3 to C30 heterocyclic group, or a combination thereof, but are not limited thereto.

The first compound may selectively absorb light in a green wavelength region. The first compound may have a maximum absorption wavelength ($\lambda_{max}$) at about 500 nm to about 600 nm and an energy bandgap of about 2.0 to about 2.5 eV.

The first compound has an axis substitution group having a planar backbone consisting of boron (B), nitrogen (N) and carbon (C), and a B—O—Si bond spread substantially vertically to the planar backbone. This structure of the first compound may decrease and/or prevent aggregation among molecules and improve film quality in a thin film state. Accordingly, light absorption characteristics of the first compound in a solution state may be prevented from being largely changed from those in the thin film state, and thus from being deteriorated.

For example, the active layer 30 may show a light absorption curve having a full width at half maximum (FWHM) of less than or equal to about 80 nm, for example of about 30 nm to about 80 nm, or for example of about 30 nm to about 65 nm. Herein, the FWHM is a width of a wavelength corresponding to a half of a maximum absorption point. As used herein, when specific definition is not otherwise provided, it may be defined by absorbance measured by UV-Vis spectroscopy. A smaller FWHM indicates selective absorption of light in a narrow wavelength region and high wavelength selectivity. Accordingly, a compound having a FWHM within the range may have high selectivity for a green wavelength region.

In the above Chemical Formula 1, the $R^1$ to $R^{15}$ and $L^1$ to $L^3$ may include combinations of the above groups, and may include, for example, groups listed in the following Table 1, but are not limited thereto.

TABLE 1

| | *—$L^1$—$R^{13}$ | *—$L^2$—$R^{14}$ | *—$L^3$—$R^{15}$ |
|---|---|---|---|
| 1 | phenyl | phenyl | phenyl |
| 2 | methyl | methyl | methyl |
| 3 | ethyl | ethyl | ethyl |
| 4 | t-butyl | t-butyl | t-butyl |
| 5 | hexyl | hexyl | hexyl |
| 6 | methyl | methyl | methyl |
| 7 | 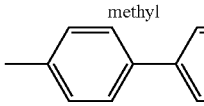 | 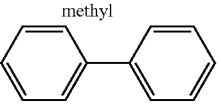 | 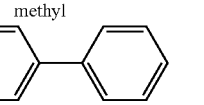 |
| 8 | 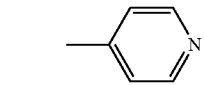 | 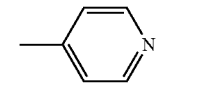 | 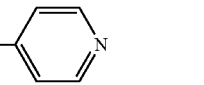 |
| 9 | 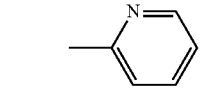 | 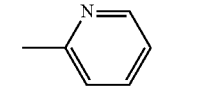 | 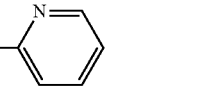 |

TABLE 1-continued

| | *—L¹—R¹³ | *—L²—R¹⁴ | *—L³—R¹⁵ |
|---|---|---|---|
| 10 | methyl | methyl | 2-thienyl |
| 11 | 1-naphthyl | 1-naphthyl | 1-naphthyl |
| 12 | o-methylphenyl | o-methylphenyl | o-methylphenyl |
| 13 | o-methoxyphenyl | o-methoxyphenyl | o-methoxyphenyl |
| 14 | 3,4,5-trimethylphenyl | 3,4,5-trimethylphenyl | 3,4,5-trimethylphenyl |
| 15 | 4-(dimethylamino)phenyl | 4-(dimethylamino)phenyl | 4-(dimethylamino)phenyl |
| 16 | isopropyl | ethyl | Ethyl |
| 17 | SiMe₃ | SiMe₃ | SiMe₃ |

Me: methyl

The first compound represented by Chemical Formula 1 discussed above may include a p-type semiconductor compound or an n-type semiconductor compound. When the first compound is a p-type semiconductor compound, a second compound as an n-type semiconductor compound may be further included, and when the first compound is an n-type semiconductor compound, a second compound as a p-type semiconductor compound may be further included.

The second compound may be a material that absorbs a part of or all of the full visible ray region, for example about 380 nm to about 780 nm.

For example, the second compound may be fullerene such as C60 or a fullerene derivative.

For example, the second compound may be thiophene or a thiophene derivative.

The thiophene derivative may be, for example, represented by the following Chemical Formula 2 or Chemical Formula 3, but is not limited thereto.

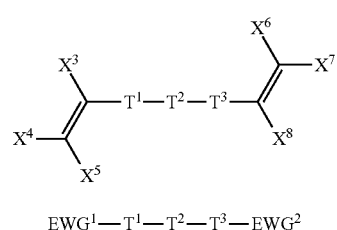

[Chemical Formula 2]

$$EWG^1 - T^1 - T^2 - T^3 - EWG^2$$

[Chemical Formula 3]

In the above Chemical Formula 2 or 3, $T^1$, $T^2$, and $T^3$ are an aromatic ring including a substituted or unsubstituted thiophene moiety, $T^1$, $T^2$, and $T^3$ are independently present or are bonded to each other, $X^3$ to $X^8$ are independently hydrogen, a substituted or unsubstituted C1 to C30 alkyl group, a substituted or unsubstituted C6 to C30 aryl group, a substituted or unsubstituted C3 to C30 heterocyclic group, a cyano group, or a combination thereof, and $EWG^1$ and $EWG^2$ are independently an electron withdrawing group.

For example at least one of $X^3$ to $X^8$ may be an electron withdrawing group.

For example at least one of $X^3$ to $X^8$ may be a cyano group.

For example $T^1$, $T^2$, and $T^3$ may be selected from groups listed in the following Group 1.

[Group 1]

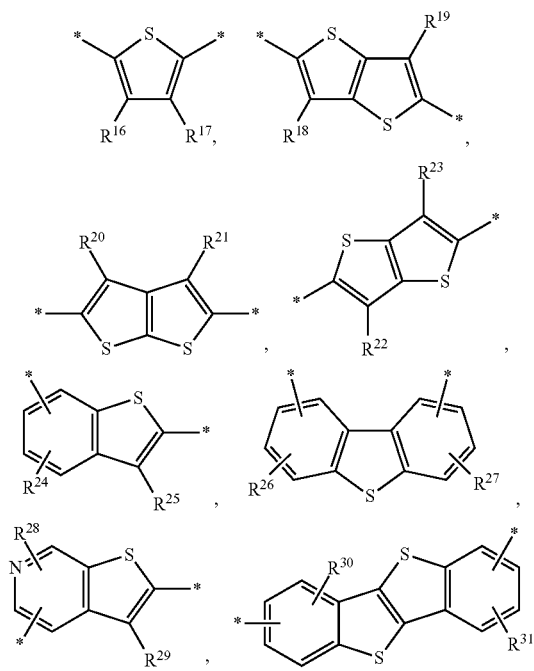

In the Group 1, $R^{16}$ to $R^{31}$ are independently hydrogen, a substituted or unsubstituted C1 to C30 alkyl group, a substituted or unsubstituted C6 to C30 aryl group, a substituted or unsubstituted C3 to C30 heteroaryl group, or a combination thereof.

For example, the thiophene derivative may be one of compounds represented by the following Chemical Formulae 2a to 2c, 3a, and 3b.

[Chemical Formula 2a]

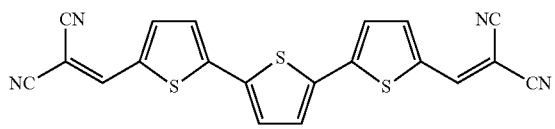

[Chemical Formula 2b]

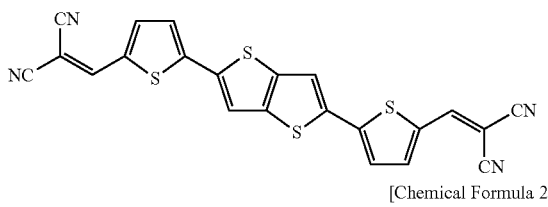

[Chemical Formula 2c]

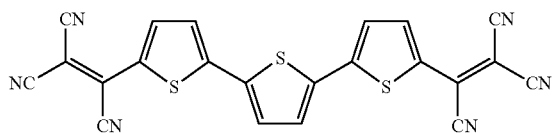

[Chemical Formula 3a]

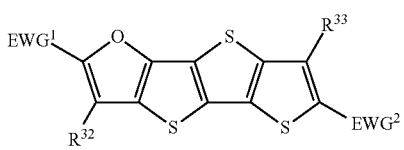

[Chemical Formula 3b]

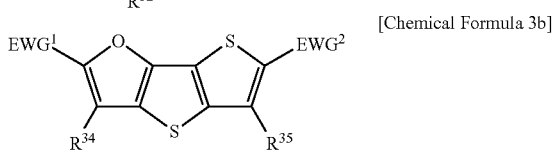

Herein, $R^{32}$ to $R^{35}$ are independently hydrogen, a substituted or unsubstituted C1 to C30 alkyl group, a substituted or unsubstituted C6 to C30 aryl group, a substituted or unsubstituted C3 to C30 heteroaryl group, or a combination thereof, and $EWG^1$ and $EWG^2$ are independently an electron withdrawing group. Examples of the electron withdrawing group may be a cyano group or a cyano-containing group.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the p-type semiconductor compound and the n-type semiconductor compound in a ratio of about 1:100 to about 100:1. The compounds may be included in a ratio ranging from about 1:50 to about 50:1 within the range, specifically, about 1:10 to about 10:1, and more specifically, about 1:about 1. When the p-type and n-type semiconductors have a composition ratio within the above ranges, an exciton may be effectively produced and a pn junction may be effectively formed.

The p-type layer may include the p-type semiconductor compound, and the n-type layer may include the n-type semiconductor compound.

The active layer 30 may have a thickness of about 1 nm to about 500 nm, and specifically, about 5 nm to about 300 nm. When the active layer 30 has a thickness within the above ranges, the active layer may effectively absorb light, effectively separate holes from electrons, and deliver them, thereby effectively improving photoelectric conversion efficiency.

In the organic photoelectronic device 100, when light enters from the first electrode 10 and/or second electrode 20, and when the active layer 30 absorbs light having a desired, or alternatively predetermined wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectronic device.

Hereinafter, an organic photoelectronic device according to another example embodiment is described.

Figure 2:
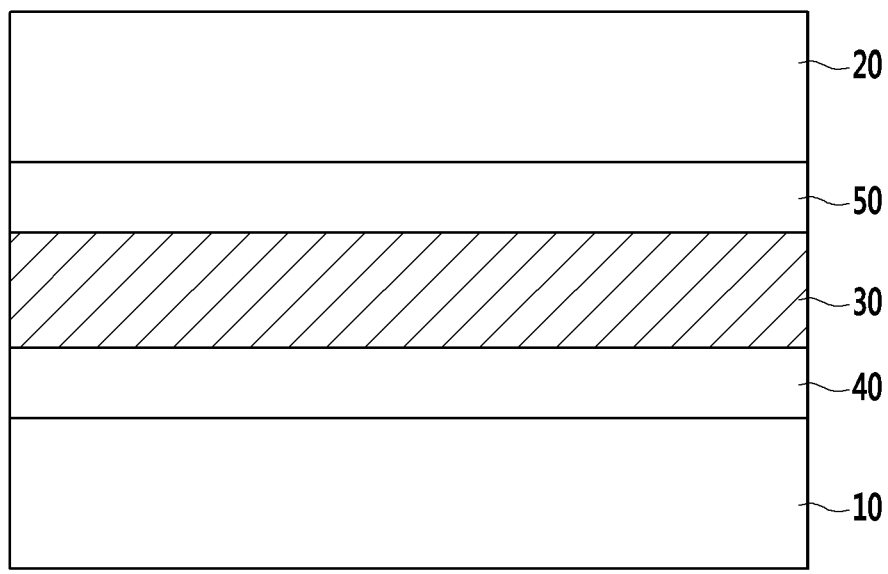
FIG. 2 is a cross-sectional view showing an organic photoelectronic device according to another example embodiment.

FIG. 2 is a cross-sectional view showing an organic photoelectronic device according to another example embodiment.

Referring to FIG. 2, an organic photoelectronic device 200 according to the example embodiment includes a first electrode 10 and a second electrode 20 facing each other, and an active layer 30 between the first electrode 10 and the second electrode 20, similarly to the above example embodiment.

However, the organic photoelectronic device 200 according to the example embodiment further includes charge auxiliary layers 40 and 50 between the first electrode 10 and the active layer 30, and the second electrode 20 and the active layer 30, unlike the above example embodiment. The charge auxiliary layers 40 and 50 may facilitate the transfer of holes and electrons separated from the active layer 30, so as to increase efficiency.

The charge auxiliary layers 40 and 50 may be at least one of a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 50 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one of, for example, poly(3,4-ethylenedioxythiophene):poly(styrene-sulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl ($\alpha$-NPD), m-MTDATA, 4,4',4"-tris(N-carbazolyl)-triphenylamine (TCTA), and a combination thereof, but is not limited thereto.

The electron blocking layer (EBL) may include one of, for example, poly(3,4-ethylenedioxythiophene):poly(styrene-sulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl ($\alpha$-NPD), m-MTDATA, 4,4',4"-tris(N-carbazolyl)-triphenylamine (TCTA), and a combination thereof, but is not limited thereto.

The electron transport layer (ETL) may include one of, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one of, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 50 may be omitted, according to at least one example embodiment.

The organic photoelectronic device may be applied to various fields, for example a solar cell, an image sensor, a photo-detector, a photo-sensor, and an organic light emitting diode (OLED), but is not limited thereto.

Hereinafter, an example of an image sensor including the organic photoelectronic device is described referring to drawings. As an example of an image sensor, an organic CMOS image sensor is described.

Figure 3:
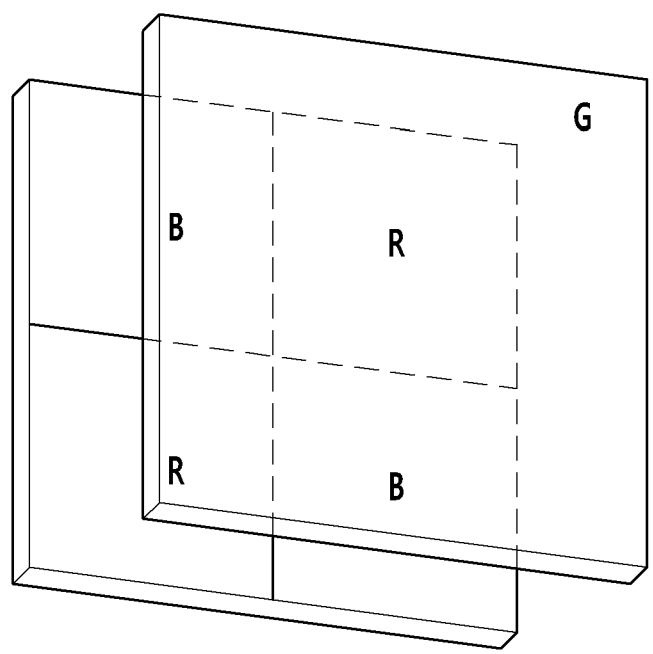
FIG. 3 is a schematic top plan view showing an organic CMOS image sensor according to at least one example embodiment.
Figure 4:
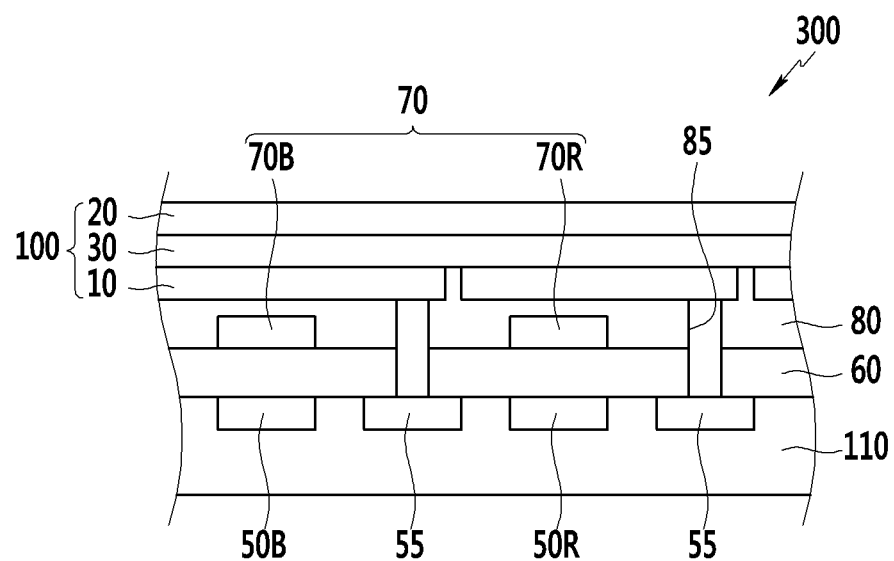
FIG. 4 is a cross-sectional view showing the organic CMOS image sensor of FIG. 3.

FIG. 3 is a schematic top plan view of an organic CMOS image sensor according to at least one example embodiment, and FIG. 4 is a cross-sectional view of the organic CMOS image sensor of FIG. 3.

Referring to FIGS. 3 and 4, an organic CMOS image sensor 300 according to at least one example embodiment includes a semiconductor substrate 110 integrated with photo-sensing devices 50B and 50R, a transmission transistor (not shown), a charge storage 55, a lower insulation layer 60, a color filter layer 70, an upper insulation layer 80, and an organic photoelectronic device 100.

The semiconductor substrate 110 may include a silicon substrate, and may be integrated with the photo-sensing device 50, the transmission transistor (not shown), and the charge storage 55. The photo-sensing devices 50R and 50B may include photodiodes.

The photo-sensing devices 50B and 50R, the transmission transistor, and/or the charge storage 55 may be integrated in each pixel or in one of the pixels, and as shown in the drawing, the photo-sensing devices 50B and 50R may be included in a blue pixel and a red pixel, and the charge storage 55 may be included in a green pixel.

The photo-sensing devices 50B and 50R sense light, the information sensed by the photo-sensing devices may be transferred by the transmission transistor, the charge storage 55 is electrically connected with the organic photoelectronic device 100, and the information of the charge storage 55 may be transferred by the transmission transistor.

In drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) may be formed on the semiconductor substrate 110. In order to decrease signal delay, the metal wire and pad may be made of or include a metal having low resistivity, for example, aluminum (Al), copper (Cu), silver (Ag), and alloys thereof, but are not limited thereto. Further, the metal wire and pad are not limited to the structure, and the metal wire and pad may be positioned under the photo-sensing devices 50B and 50R.

The lower insulation layer 60 is formed on the metal wire and the pad. The lower insulation layer 60 may be made of or include an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter 70 is formed on the lower insulation layer 60. The color filter 70 includes a blue filter 70B formed in the blue pixel and a red filter 70R filled in the red pixel. In the example embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 may be formed on the color filter 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The organic photoelectronic device 100 is formed on the upper insulation layer 80. The organic photoelectronic device 100 includes the first electrode 10, the active layer 30, and the second electrode 120 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectronic devices selectively absorbing light in a green wavelength region are stacked, and a size of an image sensor may be thereby decreased and a down-sized image sensor may be realized.

As described above, the first compound represented by the above Chemical Formula 1 as a p-type or n-type semiconductor compound is prevented from being aggregated in a thin film state, and light absorption characteristics depending on a wavelength may be maintained. Accordingly, green wavelength selectivity may be maintained, and crosstalk caused by unnecessary absorption light in a wavelength region except green may be decreased while increasing sensitivity.

In FIG. 4, the organic photoelectronic device 100 of FIG. 1 is included, but it is not limited thereto, and thus the organic photoelectronic device 200 of FIG. 2 may be applied in the same manner.

Figure 5:
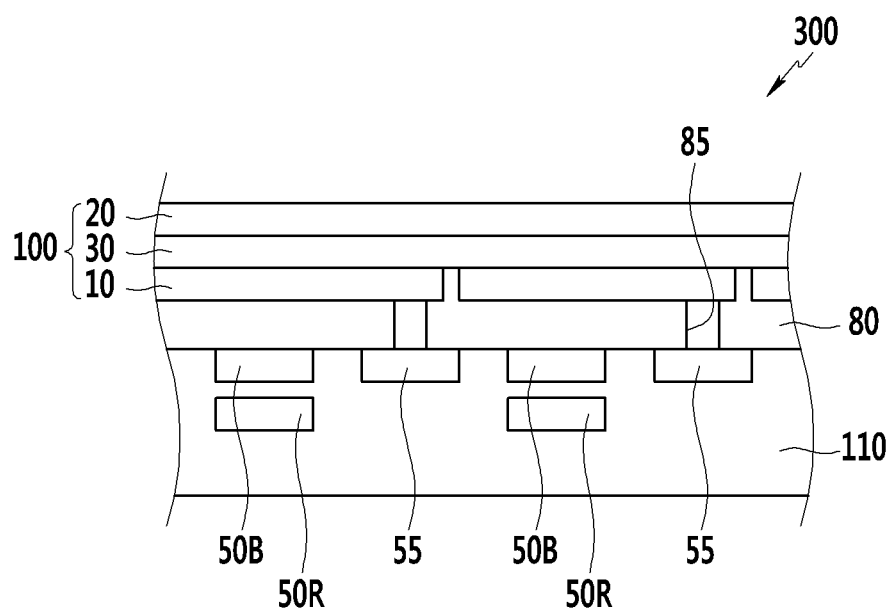
FIG. 5 is a schematic cross-sectional view showing an organic CMOS image sensor according to another example embodiment.

FIG. 5 is a schematic cross-sectional view showing an organic CMOS image sensor according to another example embodiment.

The organic CMOS image sensor 300 according to at least one example embodiment includes a semiconductor substrate 110 integrated with photo-sensing devices 50B and 50R, a transmission transistor (not shown), a charge storage 55, an insulation layer 80, and an organic photoelectronic device 100, similarly to the above example embodiment illustrated in FIG. 4.

However, the organic CMOS image sensor 300 according to the example embodiment includes the blue photo-sensing device 50B and the red photo-sensing device 50R that are stacked, and does not include a color filter layer 70, unlike the above example embodiment illustrated in FIG. 4. The blue photo-sensing device 50B and the red photo-sensing device 50R are electrically connected with the charge storage (not shown), and the information of the charge storage 55 may be transferred by the transmission transistor. The blue photo-sensing device 50B and the red photo-sensing device 50R may selectively absorb light in each wavelength region depending on a stack depth.

As described above, the organic photoelectronic devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectronic device 100 has improved green wavelength selectivity, and crosstalk caused by unnecessary absorption light in a wavelength region except green may be decreased while increasing sensitivity.

In FIG. 5, the organic photoelectronic device 100 of FIG. 1 is included, but it is not limited thereto, and thus the organic photoelectronic device 200 of FIG. 2 may be applied in the same manner.

Figure 6:
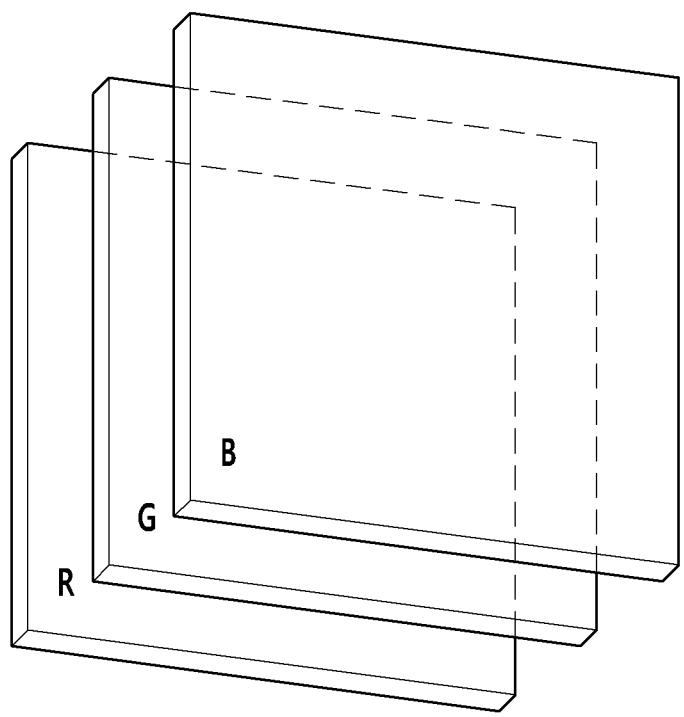
FIG. 6 is a schematic top plan view showing an organic CMOS image sensor according to another example embodiment.

FIG. 6 is a schematic top plan view of an organic CMOS image sensor according to another example embodiment.

The organic CMOS image sensor according to the example embodiment includes a green photoelectronic device G selectively absorbing light in a green wavelength region, a blue photoelectronic device B selectively absorbing light in a blue wavelength region, and a red photoelectronic device R selectively absorbing light in a green wavelength region and that are stacked.

In the drawing, the red photoelectronic device R, the green photoelectronic device G, and the blue photoelectronic device B are sequentially stacked, but the stack order may be changed without limitation.

The green photoelectronic device may be the above organic photoelectronic device 100, the blue photoelectronic device may include electrodes facing each other with an active layer therebetween and including an organic material selectively absorbing light in a blue wavelength region, and the red photoelectronic device may include electrodes facing each other with an active layer therebetween and including an organic material selectively absorbing light in a red wavelength region.

As described above, the organic photoelectronic device selectively absorbing light in a red wavelength region, the organic photoelectronic device selectively absorbing light in a green wavelength region, and the organic photoelectronic device selectively absorbing light in a blue wavelength region are stacked, and thereby a size of an image sensor may be decreased and a down-sized image sensor may be realized.

In FIG. 6, the organic photoelectronic device 100 of FIG. 1 is included, but it is not limited thereto, and thus the organic photoelectronic device 200 of FIG. 2 may be applied in the same manner.

The image sensor may be applied to, or used in, various electronic devices, for example a mobile phone, a digital camera, and the like, but is not limited thereto.

Hereinafter, the example embodiments are illustrated in more detail with reference to examples. However, the example embodiments are not limited thereto.

SYNTHESIS EXAMPLES

Synthesis Example 1

[Chemical Formula 1a]

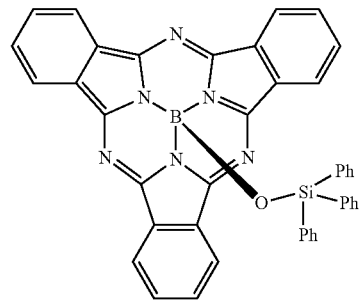

20.0 g of boron sub-phthalocyanine chloride (Sigma-Aldrich Co., Ltd.), 32.0 g of triphenylsilanol (Dong Kyung Co., Ltd.), and 14.8 g of silver trifluoromethanesulfonate (Dong Kyung Co., Ltd) are heated and refluxed in 150 ml of dry toluene for 15 hours. Then, 200 ml of methylene chloride is added thereto, the mixture is filtered, and the filtered solution is concentrated under a reduced pressure and purified through silica gel column chromatography, obtaining 13.5 g of a compound represented by the above Chemical Formula 1a. The compound represented by the above Chemical Formula 1a is further purified through sublimation, and then applied to a post-described organic photoelectronic device.

Figure 7:
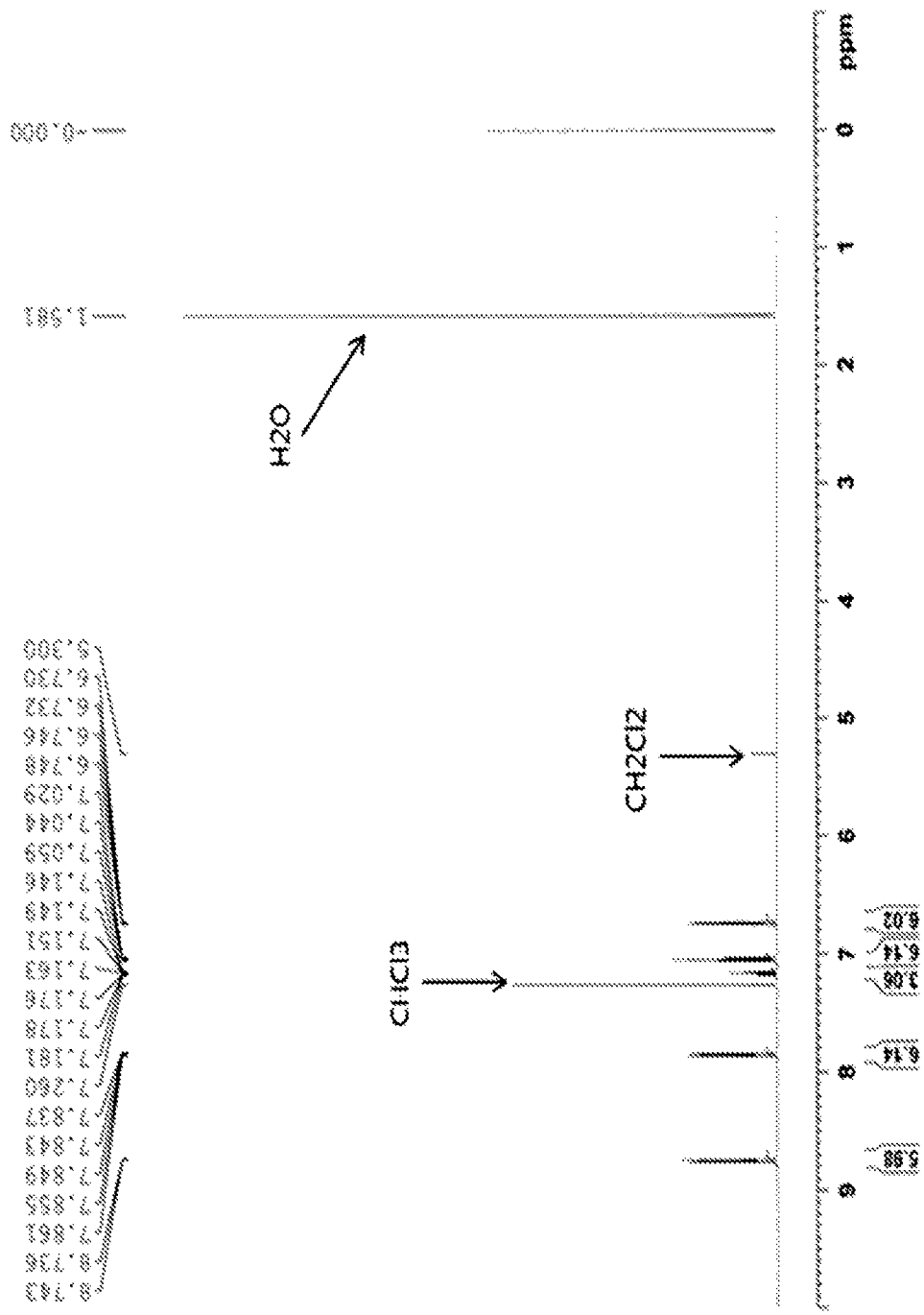
FIG. 7 shows NMR data of the compound represented by Chemical Formula 1a according to Synthesis Example 1, according to at least one example embodiment.

NMR data (BRUKER, 500 MHz) of the compound represented by the above Chemical Formula 1a is provided in FIG. 7.

FIG. 7 shows NMR data of the compound represented by Chemical Formula 1a according to Synthesis Example 1.

Synthesis Example 2

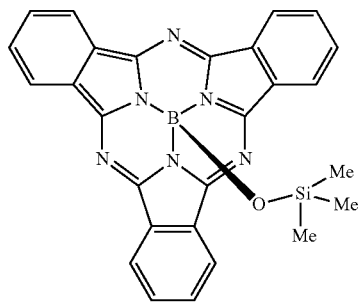

[Chemical Formula 1b]

4.6 g of the compound represented by the above Chemical Formula 1b is obtained according to the same synthesis method as Synthesis Example 1, except for using 23.8 g of potassium trimethyl siloxide (Sigma-Aldrich Co., Ltd.) instead of the triphenylsilanol and setting the reaction temperature at 50° C. The compound represented by the above Chemical Formula 1b is further purified through sublimation, and then applied to a post-described organic photoelectronic device.

Figure 8:
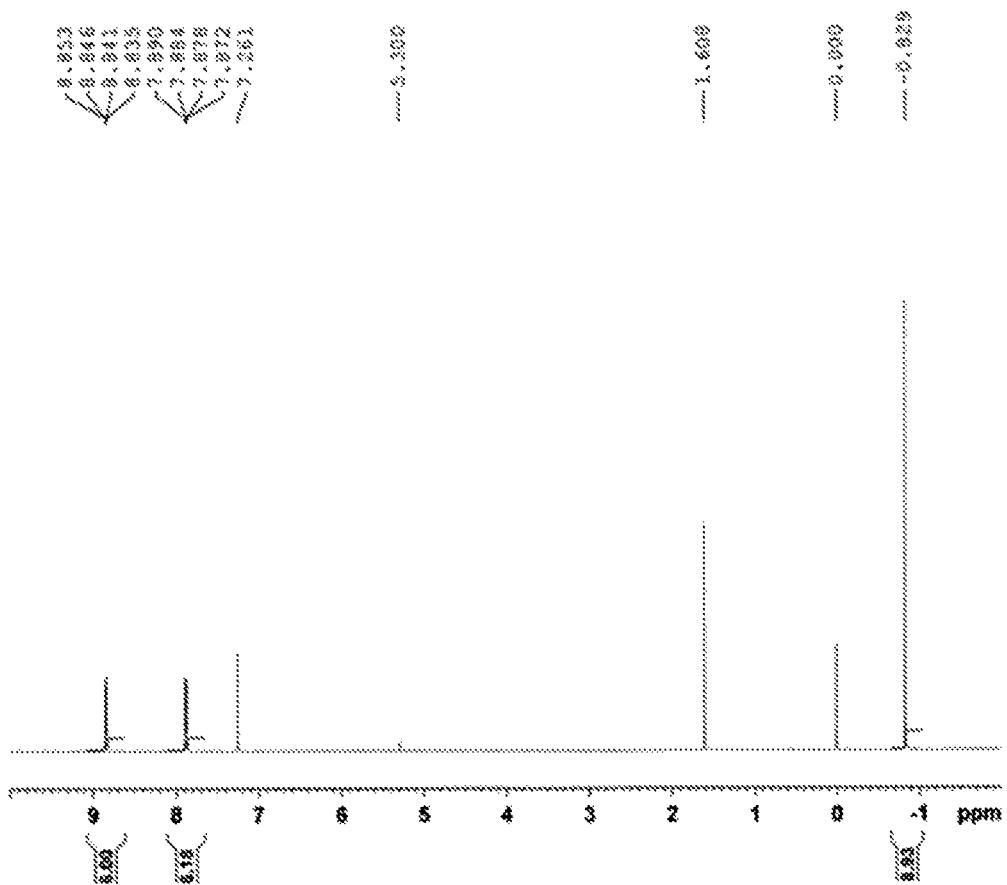
FIG. 8 shows NMR data of the compound represented by Chemical Formula 1b according to Synthesis Example 2, according to at least one example embodiment.

NMR data (BRUKER, 500 MHz) of the compound represented by the above Chemical Formula 1b is provided in FIG. 8.

FIG. 8 shows NMR data of the compound represented by Chemical Formula 1b according to Synthesis Example 2.

Comparative Synthesis Example 1

A compound represented by the following Chemical Formula A (a sublimated and refined product, LumTec, LLC) is prepared.

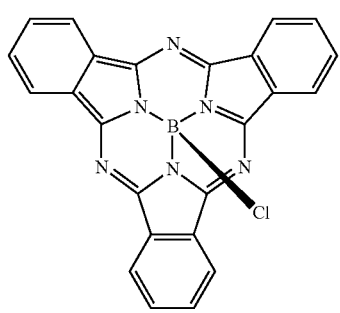

[Chemical Formula A]

Comparative Synthesis Example 2

A compound represented by the following Chemical Formula B is prepared in a method described in Angewandte Chemie, International Edition, Volume 50 Issue 15, pages 3506-3509.

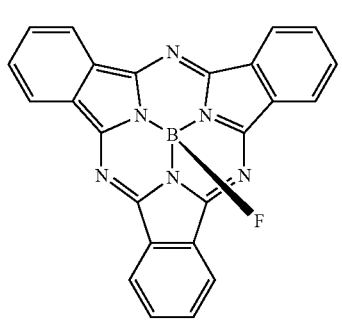

[Chemical Formula B]

Evaluation I
Evaluation 1: Light Absorption Characteristics

Light absorption characteristics of the compounds according to Synthesis Examples 1 and 2 and Comparative Synthesis Examples 1 and 2 are evaluated depending on a wavelength.

The light absorption characteristics are evaluated in both solution and thin film states of the compounds.

The light absorption characteristics in a solution state are evaluated by dissolving each compound according to Synthesis Examples 1 and 2 and Comparative Synthesis Examples 1 and 2 in a concentration of $1.0 \times 10^{-5}$ mol/L in toluene.

The light absorption characteristics in a thin film state are evaluated by thermally evaporating each compound according to Synthesis Examples 1 and 2 and Comparative Synthesis Examples 1 and 2 at a speed of 0.5-1.0 Å/s under high vacuum ($<10^{-7}$ Torr) to respectively form 70 nm-thick thin films and radiating ultraviolet (UV)-visible rays (UV-Vis) on the thin films with a Cary 5000 UV spectroscope (Varian Inc.).

Figure 9:
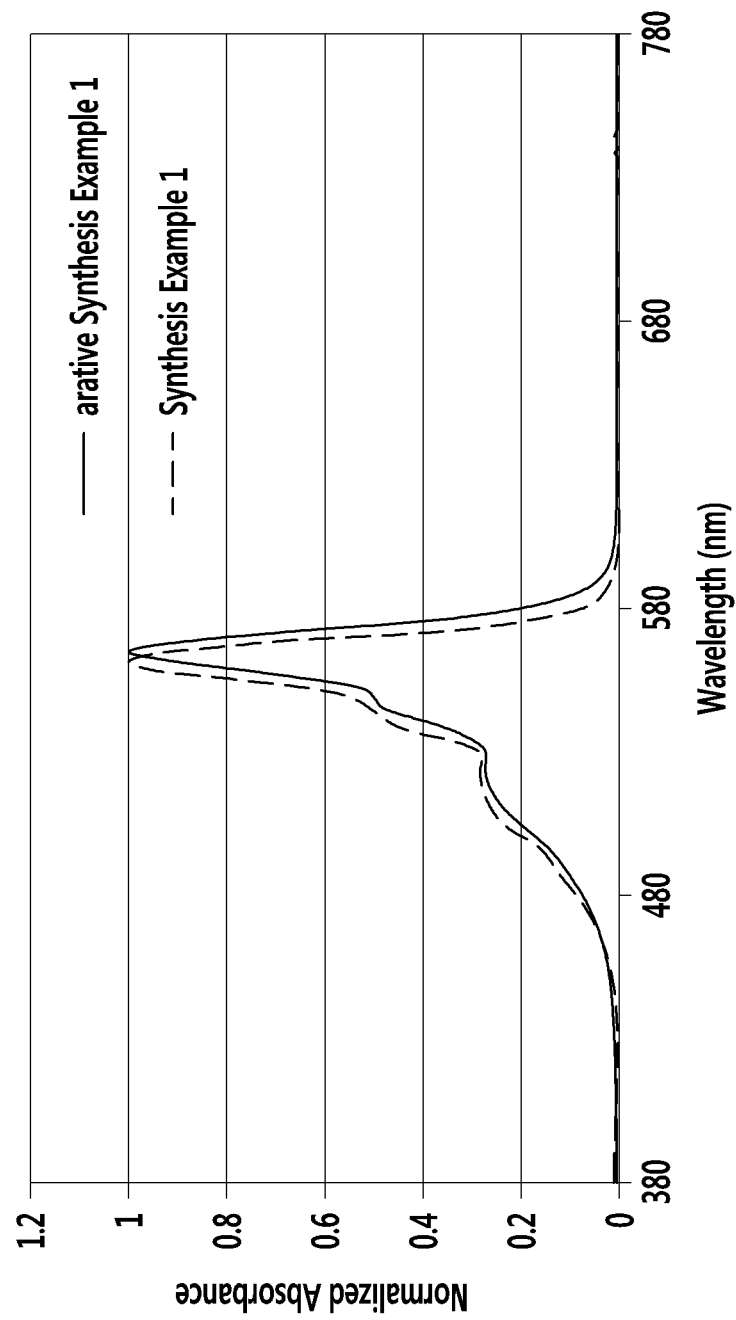
FIG. 9 is a graph showing light absorption characteristics in a solution state of the compounds according to Synthesis Example 1 and Comparative Synthesis Example 1.
Figure 10:
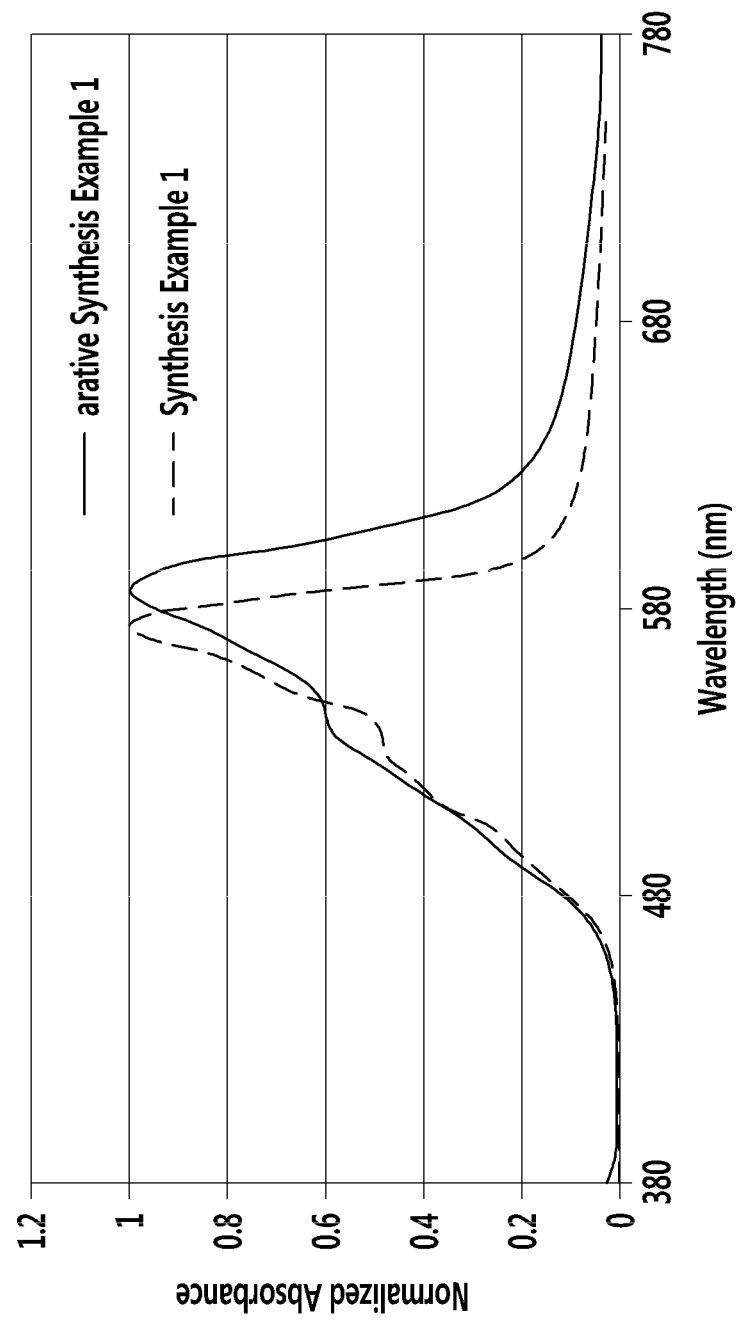
FIG. 10 is a graph showing light absorption characteristics in a thin film state of the compounds according to Synthesis Example 1 and Comparative Synthesis Example 1.

The results are provided in FIGS. 9 and 10 and Table 2.

FIG. 9 is a graph showing light absorption characteristics in a solution state of the compounds according to Synthesis Example 1 and Comparative Synthesis Example 1, and FIG. 10 is a graph showing light absorption characteristics in a thin film state of the compounds according to Synthesis Example 1 and Comparative Synthesis Example 1.

TABLE 2

| | $\lambda_{max}$ (nm) | | FWHM (nm) | | Energy level | |
|---|---|---|---|---|---|---|
| | solution | thin film | solution | thin film | HOMO (eV) | LUMO (eV) |
| Synthesis Example 1 | 562 | 575 | 29 | 46 | 5.6 | 3.5 |
| Synthesis Example 2 | 561 | 575 | 29 | 63 | 5.5 | 3.4 |
| Comparative Synthesis Example 1 | 565 | 587 | 23 | 81 | 5.6 | 3.6 |
| Comparative Synthesis Example 2 | 562 | 582 | 29 | 83 | 5.5 | 3.4 |

Referring to FIG. 9 and Table 2, the compounds according to Synthesis Examples 1 and 2 show similar or same light absorption characteristics to those of the compounds according to Comparative Synthesis Examples 1 and 2 in a solution state.

On the contrary, referring to FIG. 10 and Table 2, the compounds according to Synthesis Examples 1 and 2 show a narrower FWHM and higher green wavelength selectivity than the compounds according to Comparative Synthesis Examples 1 and 2 in a thin film state.

Specifically, the compounds according to Comparative Synthesis Examples 1 and 2 have a light absorption curve that is widened toward a long wavelength, absorb light in a red wavelength region ranging from about 600 nm to 650 nm, and respectively have a full width at half maximum (FWHM) of about 81 nm and 83 nm, while the compound according to Synthesis Example 1 maintains light absorption characteristics in a green wavelength region and a relatively narrow FWHM of about 46 nm, and the compound according to Synthesis Example 2 maintains light absorption characteristics in a green wavelength region and has a relatively narrow full width at half maximum (FWHM) of about 63 nm. Accordingly, the compounds according to Synthesis Examples 1 and 2 show a higher green wavelength selectivity state in a thin film than the compounds according to Comparative Synthesis Examples 1 and 2.

Manufacture of Organic Photoelectronic Device

Example 1

A substantially 100 nm-thick anode is formed by sputtering ITO on a glass substrate, and then a substantially 10 nm-thick charge auxiliary layer is formed thereon by depositing a molybdenum oxide ($MoO_x$, $0<x\leq3$). Subsequently, a substantially 85 nm-thick active layer is formed on the molybdenum oxide thin film by codepositing the compound (a p-type semiconductor compound) according to Synthesis Example 1 and C60 (an n-type semiconductor compound) in a thickness ratio of 1:1. Subsequently, a substantially 80 nm-thick cathode is formed on the active layer by sputtering ITO, manufacturing an organic photoelectronic device.

Example 2

An organic photoelectronic device is manufactured according to the same method as Example 1, except for using the compound according to Synthesis Example 2 instead of the compound according to Synthesis Example 1.

Comparative Example 1

An organic photoelectronic device is manufactured according to the same method as Example 1, except for using the compound according to Comparative Synthesis Example 1 instead of the compound according to Synthesis Example 1.

Evaluation II

External quantum efficiency (EQE) of the organic photoelectronic devices according to Examples 1 and 2 and Comparative Example 1 depending on a wavelength are evaluated.

The external quantum efficiency is measured by using an IPCE measurement system (McScience Co., Ltd., Korea). First of all, the IPCE measurement system is calibrated by using a Si photodiode (Hamamatsu Photonics K.K., Japan) and mounted on the organic photoelectronic devices according to Examples 1 and 2 and Comparative Example 1, and their external quantum efficiency is measured at a wavelength ranging from about 350 to 750 nm.

The results are provided in Table 3. Table 3 provides external quantum efficiency (EQE) at a maximum absorption wavelength when a voltage of −3 V is applied.

TABLE 3

|  | EQE (%) |
| --- | --- |
| Example 1 | 60 |
| Example 2 | 65 |
| Comparative Example 1 | 52 |

Referring to Table 3, the organic photoelectronic devices according to Examples 1 and 2 show improved external quantum efficiency compared with the organic photoelectronic device according to Comparative Example 1.

Evaluation III

The external quantum efficiency of the organic photoelectronic devices according to Example 1 and Comparative Example 1 measured in Evaluation II is normalized. Subsequently, in the normalized external quantum efficiency graph depending on a wavelength, the width of a wavelength corresponding to a half of maximum external quantum efficiency, that is, a full width at half maximum (FWHM), of the external quantum efficiency is evaluated.

Figure 11:
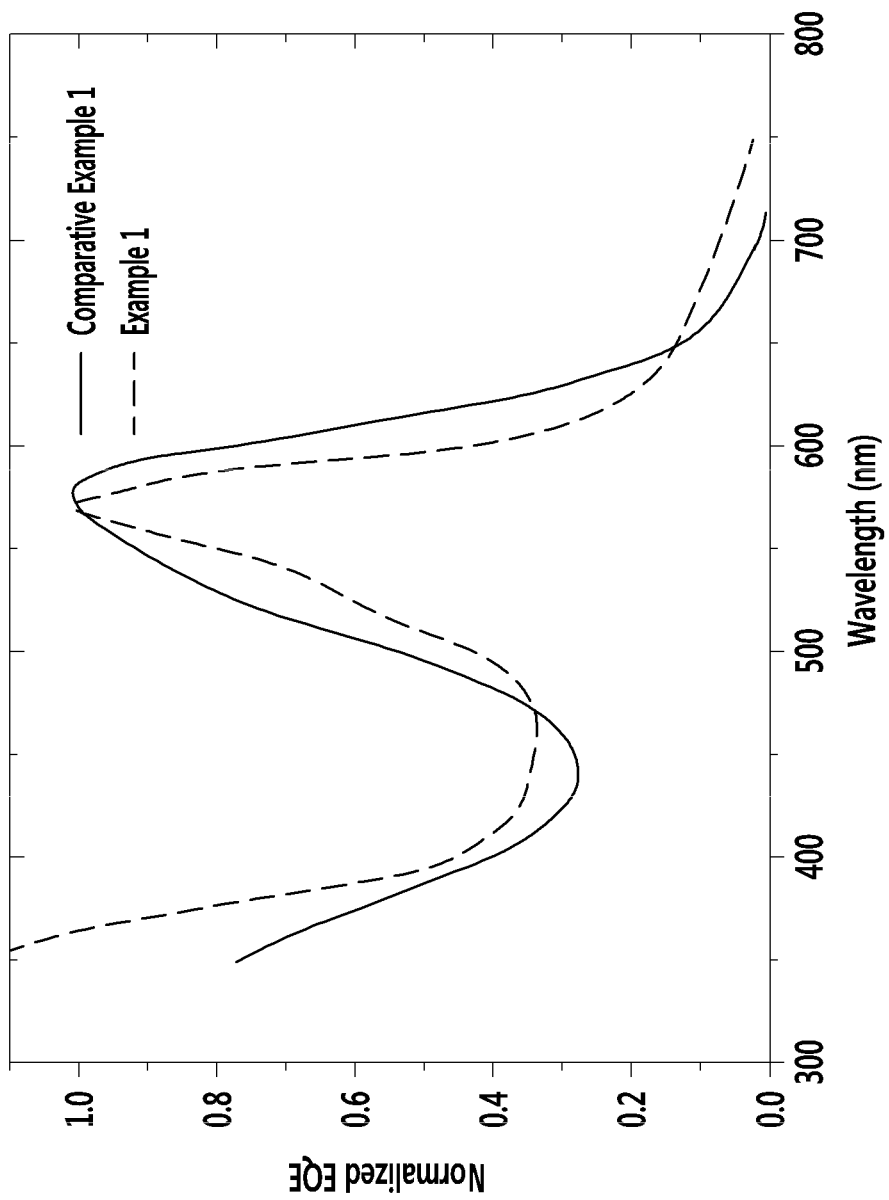
FIG. 11 is a graph showing external quantum efficiency (EQE) depending on a wavelength of the organic photoelectronic devices according to Example 1 and Comparative Example 1.

The results are shown in FIG. 11 and Table 4.

TABLE 4

|  | FWHM (nm) (normalized EQE) |
| --- | --- |
| Example 1 | 85 |
| Comparative Synthesis Example 1 | 120 |

FIG. 11 is a graph showing the external quantum efficiency (EQE) of the organic photoelectronic devices according to Example 1 and Comparative Example 1 depending on a wavelength.

Referring to FIG. 11 and Table 4, the organic photoelectronic device according to Example 1 shows external quantum efficiency (EQE) having a narrower full width at half maximum (FWHM) in a wavelength region ranging from about 500 nm to about 600 nm than the organic photoelectronic device according to Comparative Example 1. Accordingly, the organic photoelectronic device according to Example 1 shows a higher wavelength selectivity regarding the green wavelength region than the organic photoelectronic device according to Comparative Example 1 in normalized external quantum efficiency.

Evaluation IV

Crosstalk of an image sensor manufactured by respectively applying the organic photoelectronic devices according to Example 1 and Comparative Examples 1 and 2 is evaluated.

The following crosstalk evaluation is performed as follows.

Each compound according to Synthesis Example 1 and Comparative Synthesis Examples 1 and 2 and C60 in a ratio of 1:1 are respectively formed as a layer, and n and k are obtained by using spectroscopic ellipsometry. The n and k values and photoelectric conversion efficiency of a silicon photodiode and an organic photoelectronic device are used to obtain spectrum sensitivity of red, green, and blue elements having a structure shown in FIG. 4 by using an FDTD (finite difference time domain). Herein, a wavelength region is divided into three regions of 440-480 nm (blue), 520-560 nm (green), and 590-630 nm (red), and the sensitivities of each of the three regions are compared relatively to each other. In other words, when the integral of a sensitivity curve of a blue element in the 440-480 nm is arbitrarily defined as 100, the integrals of the sensitivity curves of the red and green elements in the 440-480 nm are evaluated with respect to the arbitrarily defined level of 100 for the blue element. This value is a crosstalk of the red and green elements regarding the blue region in the 440-480 nm range. The same process is performed regarding the 520-560 nm range and the 590-630 nm range to obtain each crosstalk therein. Lastly, the 6 values are averaged to obtain all crosstalk.

The results are provided in Table 5.

TABLE 5

|  | Comparative Example 1 | | | Comparative Example 2 | Example 1 | | |
|---|---|---|---|---|---|---|---|
|  | R device | G device | B device |  | R device | G device | B device |
| 440-480 nm | 8.05 | 35.94 | 100.00 |  | 8.05 | 37.00 | 100.00 |
| 520-560 nm | 5.18 | 100.00 | 8.19 |  | 7.13 | 100.00 | 11.24 |
| 590-630 nm | 100.00 | 143.84 | 12.84 |  | 100.00 | 50.96 | 12.86 |
| Average crosstalk |  | 35.7 (%) |  | 36.5 (%) |  | 21.2(%) |  |

In Table 5, the crosstalk in each pixel indicates a ratio of unnecessarily inflowing light other than the light of a particular wavelength region into each pixel when light in the wavelength regions of 590-630 nm, 520-560 nm, and 440-480 nm inflow 100% into the red pixel (R), green pixel (G), and blue pixel (B), and the average crosstalk may be defined as an average of a ratio of unnecessarily inflowing light into the red pixel (R) other than light of a red wavelength region, a ratio of unnecessarily inflowing light into the green pixel (G) other than light of a green wavelength region, and a ratio of unnecessarily inflowing light into the blue pixel (B)) other than light of a blue wavelength region.

Referring to Table 5, the organic photoelectronic device according to Example 1 shows a largely decreased average crosstalk compared with the organic photoelectronic devices according to Comparative Examples 1 and 2.

While the above example embodiments has been described in connection with what is presently considered to be practical exemplary embodiments, it is to be understood that the example embodiments are not limited to the disclosed embodiments, but, on the contrary, is intended to cover various modifications and equivalent arrangements included within the spirit and scope of the appended claims.

What is claimed is:

1. An organic photoelectronic device comprising:
a first electrode and a second electrode facing each other, and
an active layer between the first electrode and the second electrode,
wherein the active layer includes a first compound represented by the following Chemical Formula 1:

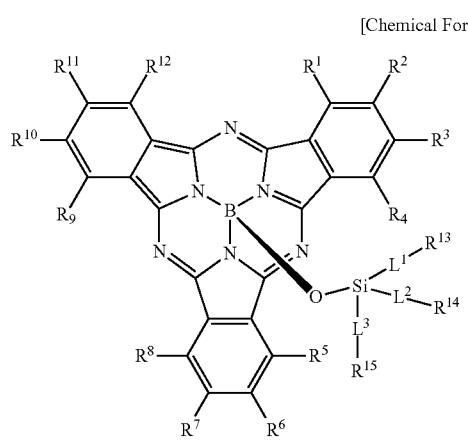

[Chemical Formula 1]

wherein
$R^1$ to $R^{12}$ are independently hydrogen or a monovalent organic group,
$R^1$ to $R^{12}$ are independently present or form a ring,
$L^1$ to $L^3$ are independently a single bond or a divalent organic group, and
$R^{13}$ to $R^{15}$ are independently a substituted or unsubstituted C1 to C30 alkyl group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group, a substituted or unsubstituted C6 to C30 arylamine group, a substituted or unsubstituted silyl group, or a combination thereof.

2. The organic photoelectronic device of claim 1, wherein $R^1$ to $R^{12}$ are independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C1 to C30 aryloxy group, a thio group, an alkylthio group, an arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, or a combination thereof, and
$L^1$ to $L^3$ are independently a single bond, a substituted or unsubstituted C1 to C30 alkylene group, a substituted or unsubstituted C6 to C30 arylene group, a divalent substituted or unsubstituted C3 to C30 heterocyclic group, or a combination thereof.

3. The organic photoelectronic device of claim 1, wherein the first compound is configured to selectively absorb light in a green wavelength region.

4. The organic photoelectronic device of claim 1, wherein the first compound has a maximum absorption wavelength ($\lambda_{max}$) of about 500 nm to about 600 nm.

5. The organic photoelectronic device of claim 1, wherein the active layer further comprises a second compound configured to absorb light in a visible wavelength region.

6. The organic photoelectronic device of claim 5, wherein the second compound comprises fullerene or a fullerene derivative.

7. The organic photoelectronic device of claim 5, wherein the second compound comprises thiophene or a thiophene derivative.

8. The organic photoelectronic device of claim 1, wherein a light absorption curve of the active layer has a full width at half maximum (FWHM) of less than or equal to about 80 nm.

9. The organic photoelectronic device of claim 1, wherein at least one of the first electrode and the second electrode are a transparent electrode.

10. An image sensor comprising the organic photoelectronic device of claim 1.

11. The image sensor of claim 10, comprising a semiconductor substrate integrated with a plurality of first photo-sensing devices configured to sense light in a blue wavelength region and a plurality of second photo-sensing devices configured to sense light in a red wavelength region, wherein the organic photoelectronic device is on the semiconductor substrate and is configured to selectively absorb light in a green wavelength region.

12. The image sensor of claim 11, wherein the first photo-sensing devices and the second photo-sensing devices are stacked in a substantially perpendicular direction to the semiconductor substrate.

13. The image sensor of claim 11, further comprising:
- a color filter layer between the semiconductor substrate and the organic photoelectronic device,
- a blue filter configured to selectively absorb light in a blue wavelength region, and
- a red filter configured to selectively absorb light in a red wavelength region.

14. The image sensor of claim 10, further comprising:
- a green photoelectronic device of the organic photoelectronic device,
- a blue photoelectronic device configured to selectively absorb light in a blue wavelength region, and
- a red photoelectronic device configured to selectively absorb light in a red wavelength region, the blue photoelectronic device and the red photoelectronic device being stacked on each other.

* * * * *